(12) United States Patent
Seyfried

(10) Patent No.: US 9,372,334 B2
(45) Date of Patent: Jun. 21, 2016

(54) MICROSCOPE AND METHOD FOR FLUORESCENCE IMAGING MICROSCOPY

(75) Inventor: Volker Seyfried, Nussloch (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 599 days.

(21) Appl. No.: 13/495,538

(22) Filed: Jun. 13, 2012

(65) Prior Publication Data

US 2012/0320184 A1  Dec. 20, 2012

(30) Foreign Application Priority Data

Jun. 17, 2011 (DE) .......................... 10 2011 105 181

(51) Int. Cl.
| | |
|---|---|
| *G01N 21/64* | (2006.01) |
| *H04N 7/18* | (2006.01) |
| *G02B 21/36* | (2006.01) |
| *G02B 21/16* | (2006.01) |

(52) U.S. Cl.
CPC .......... *G02B 21/365* (2013.01); *G01N 21/6408* (2013.01); *G01N 21/6458* (2013.01); *G02B 21/16* (2013.01)

(58) Field of Classification Search
USPC .......................................................... 348/79
See application file for complete search history.

(56) References Cited

U.S. PATENT DOCUMENTS

| | | | | |
|---|---|---|---|---|
| 5,181,234 A * | 1/1993 | Smith | .............................. | 378/87 |
| 5,252,834 A | 10/1993 | Lin | | |
| 6,687,000 B1 * | 2/2004 | White | ................ | G01N 21/6408 356/300 |
| 7,675,045 B1 * | 3/2010 | Werner et al. | ............... | 250/458.1 |
| 8,097,864 B2 * | 1/2012 | Tearney | ............. | G01N 21/6458 250/459.1 |
| 2002/0176535 A1 * | 11/2002 | Dixon et al. | ...................... | 378/62 |
| 2007/0057211 A1 * | 3/2007 | Bahlman et al. | ............... | 250/584 |
| 2008/0037008 A1 * | 2/2008 | Shepard et al. | .................. | 356/73 |
| 2008/0192129 A1 * | 8/2008 | Walker et al. | ............... | 348/231.2 |
| 2010/0309464 A1 * | 12/2010 | Treado et al. | ................. | 356/301 |
| 2012/0133756 A1 * | 5/2012 | Levin et al. | ..................... | 348/79 |
| 2013/0057869 A1 * | 3/2013 | Cotte et al. | .................... | 356/457 |

FOREIGN PATENT DOCUMENTS

| | | |
|---|---|---|
| DE | 27 47 409 A1 | 4/1978 |
| DE | 19906757 A1 | 12/1999 |
| DE | 100 38 080 A1 | 2/2002 |

(Continued)

OTHER PUBLICATIONS

Vereb, G. et al., Temporally and Spectrally Resolved Imaging Microscopy of Lanthanide Chelates, Biophysical Journal, May 1998, pp. 2210-2222, vol. 74.

(Continued)

*Primary Examiner* — Dave Czekaj
*Assistant Examiner* — Mohammad J Rahman
(74) *Attorney, Agent, or Firm* — Patentbar International, P.C.

(57) ABSTRACT

A microscope for fluorescence imaging microscopy, in particular for wide-field fluorescence microscopy, including a pulsed light source (1) and an imaging detector (11), is characterized in that means for gating are provided, and in that the gating causes the light source (1) and the detector (11) to be synchronized in order to suppress reflected/scattered light such that suitable fluorescence components are used for evaluation and unsuitable components are rejected. Furthermore, a method is used to perform fluorescence imaging microscopy using the microscope according to the present invention.

17 Claims, 4 Drawing Sheets

(56) References Cited

FOREIGN PATENT DOCUMENTS

| | | |
|---|---|---|
| DE | 10336080 A1 | 3/2005 |
| DE | 10 2004 039 035 A1 | 10/2005 |
| DE | 102008018475 A1 | 10/2009 |
| WO | 02/068942 A2 | 9/2002 |

OTHER PUBLICATIONS

Martyshkin, D. V. et al., Effective Suppression of Fluorescence Light in Raman Measurements Using Ultrafast Time Gated Charge Coupled Device Camera, Review of Scientific Instruments, Mar. 2004, pp. 630-635, vol. 75, No. 3.

* cited by examiner

MICROSCOPE AND METHOD FOR FLUORESCENCE IMAGING MICROSCOPY

RELATED APPLICATIONS

This application claims priority to German Patent Application No. 10 2011 105 181.7 filed on Jun. 17, 2011, which is incorporated herein by reference in its entirety.

BACKGROUND OF THE INVENTION

The present invention relates to a microscope for fluorescence imaging microscopy, in particular for wide-field fluorescence microscopy, including a pulsed light source and an imaging detector. The invention also relates to a corresponding method, in particular for applying the microscope of the present invention.

Very generally, the present invention concerns fluorescence microscopy, and specifically wide-field fluorescence microscopy.

Wide-field fluorescence microscopy is of great importance in biological and medical research. While in classical fluorescence microscopy, the sample is illuminated more or less point by point, in wide-field microscopy, the sample is illuminated over a large area and imaged by an objective, so that the point spread function (PSF) of the overall system is determined only by the (detection) PSF of the objective. In contrast, in a confocal microscope, the incident light is focused onto the sample, so that the overall PSF is the product of the illumination PSF and the detection PSF.

In general, in wide-field fluorescence microscopes, the amount of excitation light scattered back from the sample into the detector beam path of the microscope is significantly higher than is possible in confocal microscopes, where spatial filtering is provided by the detection pinhole. In order to nevertheless be able to acquire images under satisfactory conditions, it is necessary to suppress the scattered/reflected light to a sufficient degree. To this end, wide-field fluorescence microscopes typically use barrier filters which suppress the corresponding excitation wavelengths. Usually, filter cubes are used which, in addition to the barrier filter (emission filter), also include an excitation filter for spectral filtering of the excitation light, and a dichroic as the main beam splitter, the main beam splitter assisting both the excitation filter and the emission filter.

However, the disadvantage here is that the invariable filter characteristics do not allow for spectral tuning of the excitation light. Moreover, in the case of multiple wavelength excitation, very special filters have to be used to transmit or reflect at the appropriate spectral locations, which further restricts flexibility and, given a multitude of possible spectral excitation and detection regions, requires a number of combinations so high that it cannot be implemented by the filter wheels commonly used in practice. In addition, due to the spectral width of the corresponding filters, the detection region must have a defined spectral distance from the excitation wavelength region, as a result of which excitation light which one would wish to detect in order to increase the sensitivity of the microscope is lost in the intermediate region.

For further details on confocal microscopes, reference may be made, for example, to DE 199 06 757 A1. There, the detection light is—usually—at least partially present in the form of a directed beam which passes through a pinhole. Accordingly, it is possible to use acousto-optical devices. In contrast, in wide-field microscopy, a real image is formed in the field optics, which means that light is incident at a plurality of angles at the same time, which, in turn, seems to make the use of acousto-optical devices unsuitable or even virtually impossible. This is attributable to the fact that acousto-optical devices require an enormously large optical opening and would therefore be extremely complex and expensive.

From U.S. Pat. No. 5,252,834, it is known per se to use gating in a microscope, but not for imaging purposes, and even less for suppressing reflected/scattered light during imaging. Rather, this patent is concerned with the imaging of point spectra for characterizing the chemical composition of samples (microspectrophotometry), and does not provide for the use of imaging detectors.

SUMMARY OF THE INVENTION

The object of the present invention is, in fluorescence imaging microscopes capable of wide-field fluorescence microscopy, to achieve suppression of reflected/scattered light using simple means to be able to acquire reproducible images under satisfactory conditions. The features required to achieve this should be implementable with simple means in a cost-effective manner.

With regard to the microscope according to the present invention, the above object is achieved by the features of claim 1. With regard to the method according to the present invention, the above object is achieved by the features of claim 18, using a microscope according to the present invention.

In the microscope according to the present invention, the underlying problem is solved by providing means for gating, and in that the gating causes the light source and the detector to be synchronized in order to suppress reflected/scattered light such that suitable fluorescence components are used for evaluation and unsuitable components are rejected. The method of the invention is designed accordingly.

The approach of the present invention proposes the gating of an imaging detector in microscopy in combination with pulsed light sources. However, the cameras currently commonly used in microscopy do not allow gating, and even less for all pixels simultaneously, because readout is usually performed sequentially via common readout registers. This is also not possible with the conventional CMOS chips having single-photon detection sensitivity because, although they do allow parallel readout, the readout process is far too slow to permit suitable gating in the sub-100 ns range.

On the basis of the present invention, preferably, arrays of avalanche photodiodes operated in Geiger mode (APD arrays; this type of APDs sometimes also being called "silicon photomultipliers") are used to provide imaging units which can be gated and enable suppression of reflected/scattered light in accordance with the present invention. In principle, it would also be conceivable to implement "gatable cameras" in other ways.

The present invention is based on a fluorescence microscope which operates with a pulsed light source and an imaging detector. With regard to the pulsed light source, it is advantageous for this light source to have a pulse duration on the order of, or better shorter than, the lifetime of the fluorophores to account for the fluorescence decay time. Assuming that conventional fluorescent dyes are used, it is advantageous to implement pulse durations in the range below 5 ns, preferably below 1 ns, and particularly preferably below 200 ps. The light source may be a laser, an LED, a flashlight LED, or a laser-pumped amplifying medium, etc. It is especially advantageous if the light source can be triggered. However, this is not absolutely necessary for the implementation of the teaching of the present invention.

Particularly advantageously, pulsed white-light lasers, pulsed, LEDs, pulsed OPOs, and other pulsed lasers can be used.

Detection is performed using an imaging detector which constitutes, as it were, a "gatable camera". This can be either a camera with any type of triggerable/gatable fast optical shutter in front of it, or an activatable/deactivatable imaging detector. It is also possible to use an imaging detector which, after producing the detector signal, provides suitable information indicating whether to use or reject the respective signal component.

A gatable optical shutter could be, for example, a rapidly switchable optical image intensifier which, when in the OFF state, does not amplify the light, but does so when in the ON state. It could also be a saturable optical absorber which is saturated by short pulses of light and, therefore, becomes transparent when the gate is applied.

A gatable detector could be implemented on the basis of avalanche photodiodes (APD) operated in Geiger mode. In this connection, each individual image pixel of the imaging detector is composed of a single APD operated in Geiger mode or a plurality thereof (=subarray). Application of a suitable gate voltage enables the Geiger mode of the individual APDs, thereby allowing incident photons to cause the APDs to break down, producing a corresponding electronic signal. However, this cannot happen as long as the gate is OFF, so that the detector is not active during this time.

It is also conceivable to implement a gate in a different way, for example, by short-circuiting the output of the detector, or disconnecting it from the signal lead-out line, while the gate is OFF. Externally controllable gates of a similar kind can also be implemented in other camera types, such as CMOS or CCD chips.

In principle, it is not absolutely necessary to suppress the generation of a signal when the gate is in the OFF state. It is sufficient to "conserve" the corresponding time information. In the extreme case, it is sufficient to timestamp each individual photon; i.e., to store the time of arrival for each individual photon, so as to decide in a downstream data processing unit (FPGA, DSP, etc.) whether to use or reject the photon. This does not necessarily have to be done for each individual photon. In principle, it is sufficient to record the signal waveform, or parts thereof, for each image pixel and evaluate it later.

There is some crossover between the techniques discussed above, especially because electronics are nowadays increasingly integrated. It is merely important that the imaging unit can be gated, it being preferred to provide the same (a simultaneous) gate for all image pixels, although in special cases, different temporal gate positions are also conceivable.

The decisive inventive step can be seen to lie in that the gatable imaging unit is synchronized with the pulsed light source in such a way that suitable fluorescence components are used and unsuitable components are rejected in a reproducible manner. Preferably, the light components belonging to the fluorescent light of interest are used for imaging by means of the suitable gate, regardless of how it is implemented. The components belonging to the reflected or scattered light are rejected. In certain cases, it may be useful to use the fluorescent light of a freely selectable period of time after the illumination, while other light is rejected or at least assigned or delivered to another detection channel. This may be relevant, in particular, for samples where the fluorescence lifetime permits conclusions about the local conditions inside the sample.

To implement the idea of the present invention, it is merely required that the imaging detector; i.e., the "camera", be capable of being suitably synchronized to the light source by means of its gate. This can be accomplished by providing a central trigger unit, which constitutes the master on which the light source and the camera are triggered. Conversely, it is also possible for the light source to generate the master trigger on which the camera is triggered (for example, in the case of passively mode-locked lasers), or the camera can generate the trigger from an intrinsic or externally controlled clock, and light source is then synchronized to this trigger.

Once a suitable configuration is implemented, it is easy to achieve suppression of reflected/scattered light in the microscope. In conventional microscopes, this alone helps to enable imaging of difficult samples.

This advantage makes it possible to omit the fluorescence cubes typically used in microscopes, which allows significantly greater spectral freedom than before. If a neutral beam splitter (e.g., 50:50 or 80:20; i.e., 20% light input in reflection and 80% fluorescence yield in transmission, or other splitting ratios) is used in place of the fluorescence cube, then it is possible to use any desired wavelengths simultaneously for fluorescence excitation and, in the extreme case, even to perform detection at the same wavelengths without having problems with reflected or scattered light.

However, in order to achieve the latter, particularly efficient suppression is required, which may be achieved, for example, by combining different gating methods. In addition, the use of barrier filters, notch filters, band-edge filters, graduated filters, or other filters continues to be possible The use of a polarization filter in place of the above-described neutral filter, combined with the simultaneous use of suitably polarized excitation light, also contributes to the further suppression of reflected/scattered light. However, this results in reduced detection sensitivities. It should be noted at this point that the term "suppression of reflected/scattered light" is not limited to reflection/scatter from the sample, but includes also light which may be reflected/scattered from components inside the microscope and needs to be suppressed.

It is particularly advantageous to use neutral filters; i.e., spectrally relatively flat filters, or tunable filters in combination with tunable light sources or light sources having a flat spectral distribution (e.g., white light sources), from whose spectrum the illuminating light is separated. This combination makes it possible to implement a wide-field microscope which is spectrally completely tunable and has a high sensitivity. This allows the illumination to be adjusted in an optimized manner for each individual sample, and even makes it possible to perform excitation wavelength scans. This may also be combined with spectral detection in the microscope. In the extreme case, it is even possible to record suitably combined excitation/emission spectra.

The technique according to the present invention can be used in all fluorescence microscopes having imaging units, including spinning disk microscopes, localization microscopes, TIRF microscopes, structured illumination microscopes, SPIM microscopes, etc. The technique according to the present invention may be used for both incident-light and transmitted-light fluorescence microscopy.

BRIEF DESCRIPTION OF THE DRAWINGS

The teaching of the present invention may be advantageously embodied and refined in various ways. In this regard, reference is made, on the one hand, to the claims that are subordinate to claim 1 and, on the other hand, to the following description of preferred exemplary embodiments of the present invention which makes reference to the drawing. In conjunction with the explanation of the preferred exemplary embodiments of the invention with reference to the drawing, an explanation is also given of generally preferred embodiments and refinements of the teaching. In the drawing, FIG. 1 schematically illustrates the basic design of a known conventional fluorescence microscope with a filter cube, such as is known in the art;

DETAILED DESCRIPTION OF THE PREFERRED EMBODIMENTS

Figure 1:
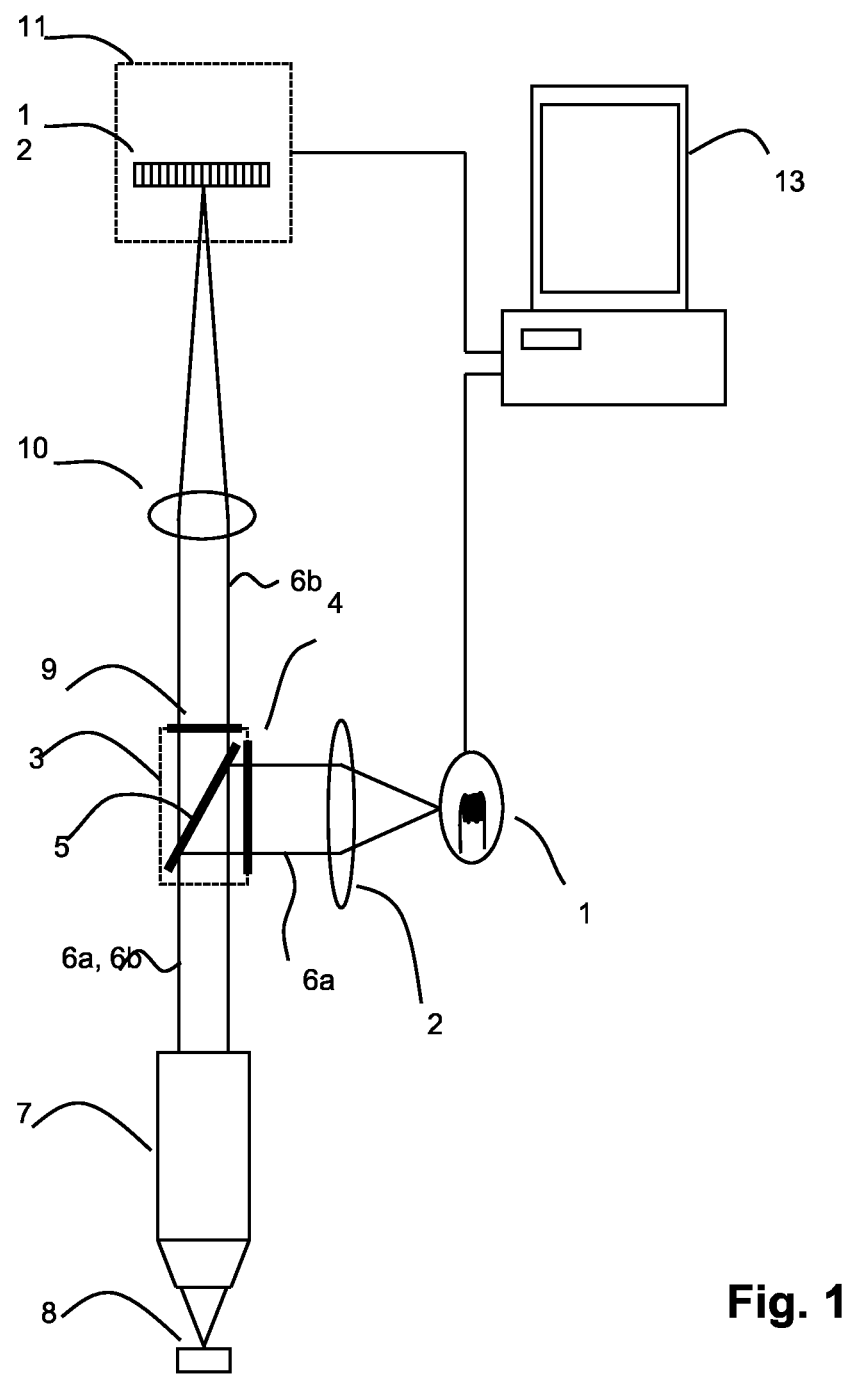

FIG. 1 shows in schematic form the basic design of a conventional fluorescence microscope, in which the excitation light is tuned by a filter cube.

In particular, the configuration shown in FIG. 1 includes an illumination unit 1 as a light source, a condenser 2 located downstream of illumination unit 1, and a filter cube 3 containing an excitation filter 4 and a dichroic beam splitter 5. Excitation light 6a passes through excitation filter 4 and is directed through an objective 7 to sample 8.

Fluorescent light/reflected light 6b coming from sample 8 passes through objective 7 and filter cube 3 to an integrated emission filter 9 and is focused by a tube lens 10 onto a detector 11, which may take the form of a camera having an integrated camera chip 12. The signals so obtained are fed to a computer 13, which includes both an image-processing unit and control unit, in particular for controlling illumination unit 1.

Figure 2:
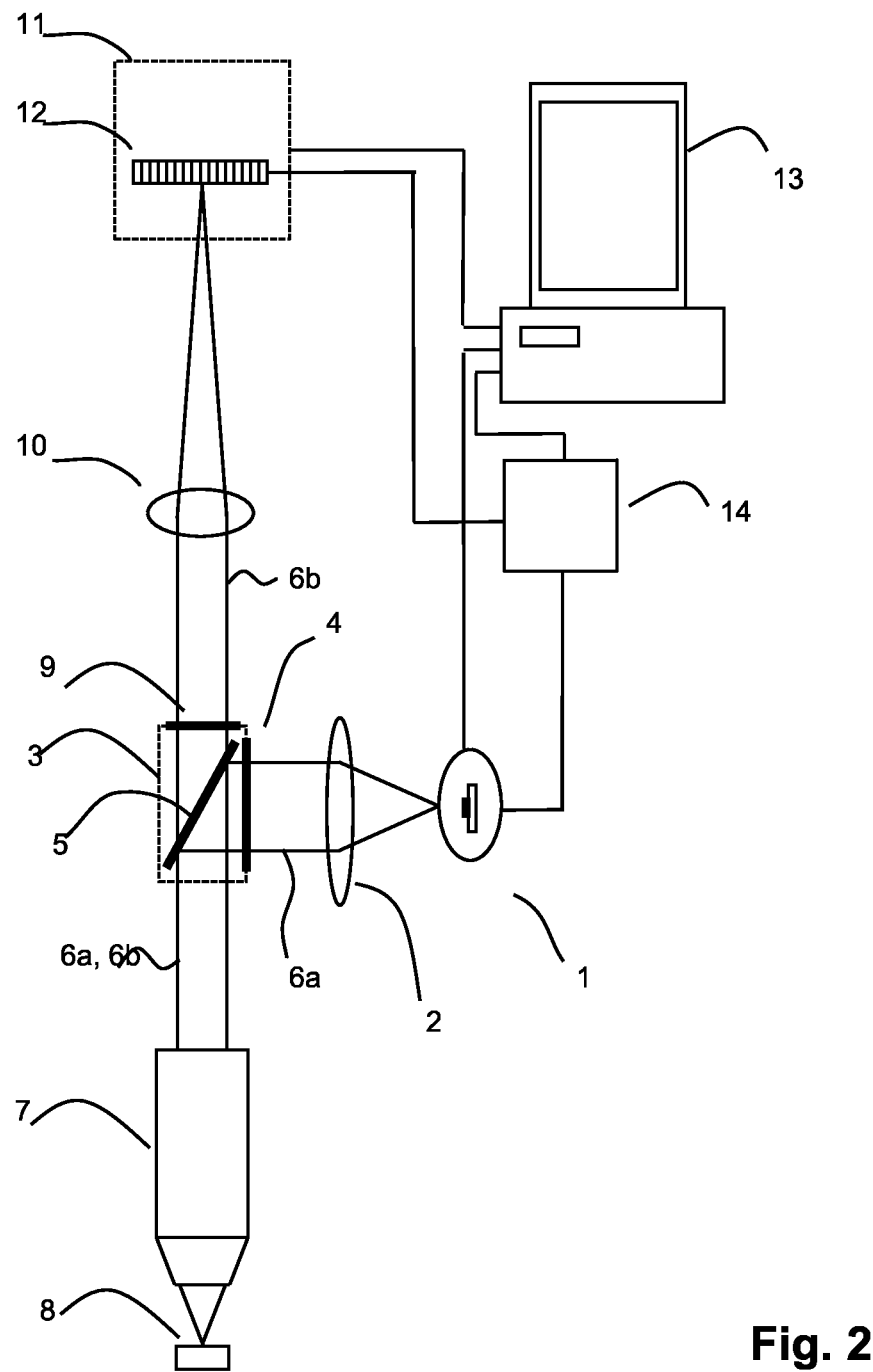
FIG. 2 shows a first exemplary embodiment of a microscope according to the present invention, where the illumination unit includes triggerable LEDs.

FIG. 2 shows a first exemplary embodiment of a configuration according to the present invention, which still uses the filter cube 3 known from the prior art. A triggerable LED is used as a triggerable illumination unit 1. In order to perform gating in accordance with the present invention, a master is provided, specifically a trigger/synchronization unit 14 which is controllable by and/or programmable via computer 13. For details on other design features which correspond to those used in the prior art illustrated in FIG. 1, reference is made to the description of FIG. 1 to avoid repetition.

Figure 3:
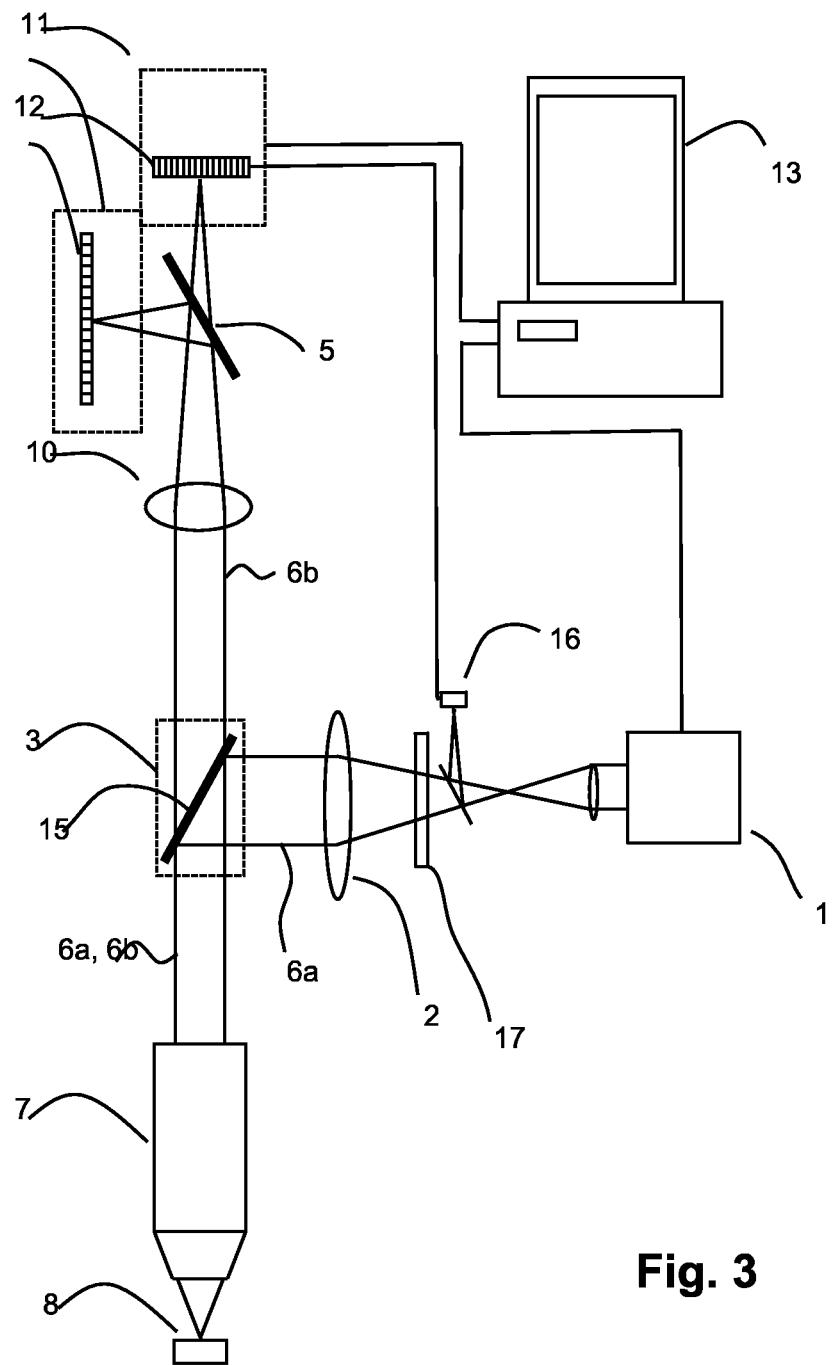
FIG. 3 shows another exemplary embodiment of a microscope according to the present invention, which uses a neutral or polarizing beam splitter.

FIG. 3 shows a further exemplary embodiment of a configuration according to the present invention, where a neutral or polarizing beam splitter 15 is used as part of or in place of a filter cube 3. Illumination unit 1 is designed as a laser, which defines the master for the gating according to the present invention. Its trigger is tapped via an optical reference sensor 16. The trigger is fed directly to gatable camera 11, which may include an integrated evaluation unit. This may make it possible to dispense with an external trigger unit.

In the exemplary embodiment shown in FIG. 3, two spectral detector units in the form of cameras 11 are provided by way of example only. A graduated filter 17 is used to extract specific spectral components from [the light of] illumination unit 1 for illumination. In this regard, it should be noted that other elements of similar functionality, for example, AOTFs, may also be used in place of graduated filter 17.

Figure 4:
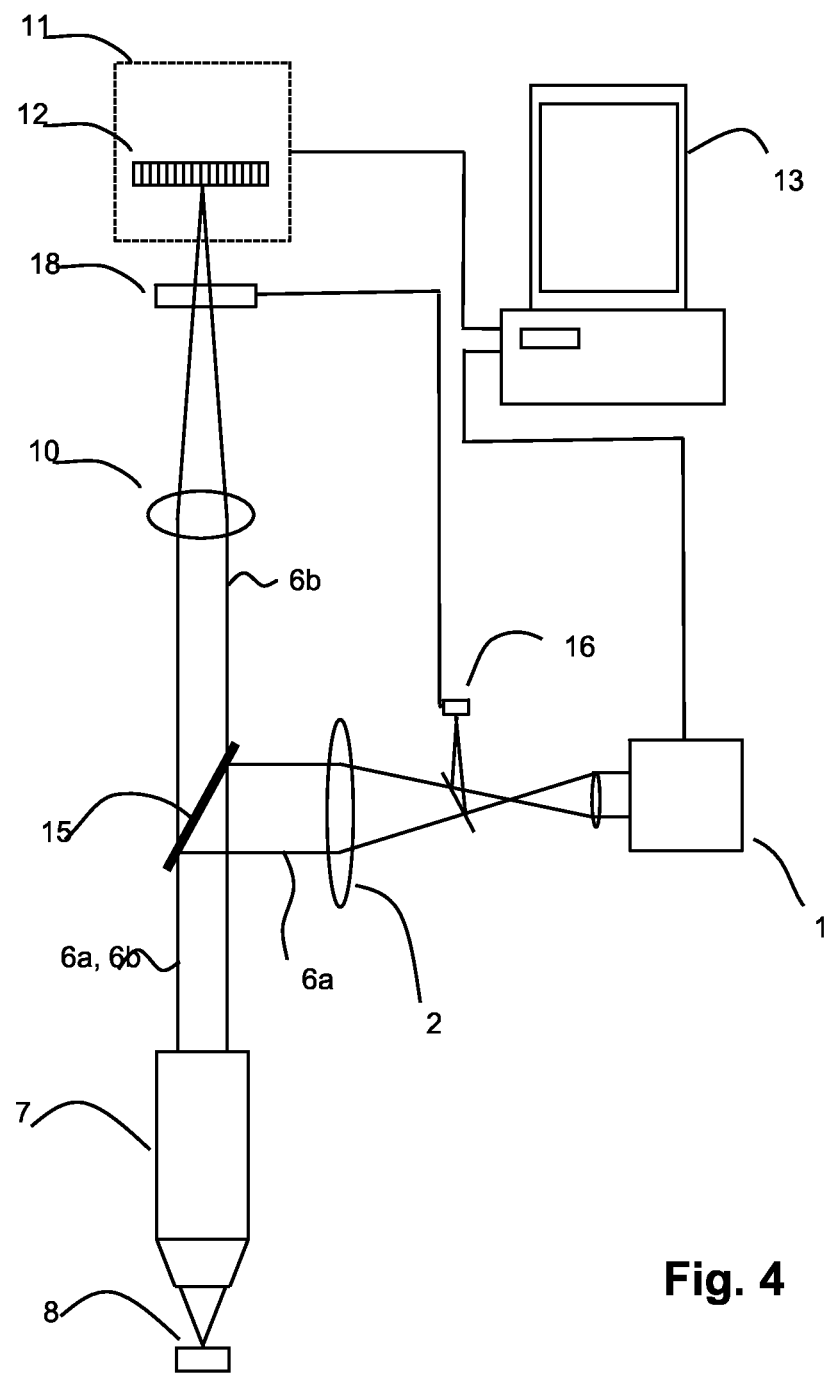
FIG. 4 shows a further exemplary embodiment of a microscope according to the present invention, which uses a fast optical shutter.

FIG. 4 shows another exemplary embodiment of a configuration according to the present invention, which is implemented using a fast optical shutter 18. In FIG. 4, it is also envisaged that in a particularly preferred embodiment of the inventive idea, neutral beam splitter 15 can be permanently installed in the microscope, as a result of which it is not, or no longer, necessary to change filter cubes.

With regard to further advantageous embodiments of the microscope according to the present invention and to avoid repetition, reference is made to the general part of the description and to the appended claims.

Finally, it should be particularly noted that the above-described exemplary embodiments of the device according to the present invention are merely intended to illustrate the claimed teaching, but not to limit it to such embodiments.

LIST OF REFERENCE NUMERALS 1 illumination unit, light source
2 condenser
3 filter cube
4 excitation filter
5 dichroic beam splitter, dichroic
6a excitation light
6b fluorescent light/reflected light
7 objective
8 sample
9 emission filter
10 tube lens
11 detector, camera
12 camera chip
13 computer, data processing unit
14 trigger/synchronization unit
15 neutral beam splitter, polarizing beam splitter
16 optical reference sensor
17 graduated filter
18 optical shutter

What is claimed is:

1. A microscope for fluorescence imaging microscopy, in particular for wide-field fluorescence microscopy, comprising:
   a pulsed light source sending excitation light via an objective to a sample;
   an imaging detector receiving fluorescent light and scattered or reflected light from the sample via the objective; and
   a synchronization unit, controllable by a computer, providing gating of the imaging detector in combination with the pulsed light source to synchronize the pulsed light source and the imaging detector to (1) suppress components of the scattered or fluorescent light, (2) allow evaluation of suitable fluorescence components of the fluorescent light, and (3) reject unsuitable fluorescence components of the fluorescent light,
   wherein the fluorescence components comprise photons and wherein a timestamp representing a time of arrival of each photon, or a record of a time of arrival of each signal waveform of an image pixel, is assigned to each photon or image pixel so as to decide in a downstream data processing unit whether each photon or image pixel is suitable for evaluation.

2. The microscope as recited in claim 1,
   wherein the synchronization unit gating allows the suitable fluorescence components belonging to a fluorescent light of interest to be fed to the imaging detector and components of the scattered or reflected light are not used for imaging.

3. The microscope as recited in claim 1,
   wherein fluorescent light of a definable time window after illumination of the sample is used for imaging, and the fluorescent light outside of the time window is not used for imaging and can be delivered to another detection channel.

4. The microscope as recited in claim 1, wherein a same or a simultaneous gate is provided for all image pixels.

5. The microscope as recited in claim 1, wherein different temporal gates or gate positions are implemented for different image pixels.

6. The microscope as recited in claim 1, wherein the synchronization unit comprises a central trigger unit which defines a master on which the pulsed light source and the detector can be triggered.

7. The microscope as recited in claim 6, wherein the pulsed light source comprises mode-locked lasers which generate a master trigger on which the detector can be triggered.

8. The microscope as recited in claim 6, wherein the detector generates a trigger to which the pulsed light source can be synchronized from an intrinsic or externally controlled clock.

9. The microscope as recited in claim 1, wherein the detector comprises a gatable camera.

10. The microscope as recited in claim 9, wherein the camera includes, or is functionally associated with, a triggerable/gatable fast optical shutter.

11. The microscope as recited in claim 10, wherein the shutter comprises a rapidly switchable optical image intensifier which amplifies light when in the ON state.

12. The microscope as recited in claim 10, wherein the shutter comprises an optical absorber which is saturated by short pulses of light and, therefore, becomes transparent when a gate signal is applied.

13. The microscope as recited in claim 1, wherein the detector is gatable to be activated or deactivated.

14. The microscope as recited in claim 1, wherein while gating is OFF, an output of the detector is short-circuited or disconnected from a signal lead-out line.

15. The microscope as recited in claim 1, wherein the detector includes arrays of avalanche photodiodes (APD) preferably operable in Geiger mode, each individual image pixel of the imaging detector being composed of a single APD or a plurality of APDs as a subarray.

16. The microscope as recited in claim 1, wherein the detector, after producing a detection signal, provides information qualifying a respective signal component as usable or not usable.

17. A method for fluorescence imaging microscopy, in particular for wide-field fluorescence microscopy, comprising:
sending excitation light from a pulsed light source via an objective to a sample;
receiving fluorescent light and scattered or reflected light at an imaging detector from the sample via the objective; and
gating the imaging detector in combination with the pulsed light source to synchronize the pulsed light source and the imaging detector to (1) suppress components of the scattered or reflected light, (2) allow evaluation of suitable fluorescence components of the fluorescent light, and (3) reject unsuitable fluorescence components of the fluorescent light,
wherein the fluorescence components comprise photons and wherein a timestamp representing a time of arrival of each photon, or a record of a time of arrival of each signal waveform of an image pixel, is assigned to each photon or image pixel so as to decide in a downstream data processing unit whether each photon or image pixel is suitable for evaluation.

* * * * *